(12) United States Patent
Kantonen et al.

(10) Patent No.: US 7,443,959 B2
(45) Date of Patent: Oct. 28, 2008

(54) SELECTIVE IRRADIATION OF SMALL TARGET AREA IN X-RAY FLUORESCENT SPECTROSCOPY

(75) Inventors: Esko Juhani Kantonen, Helsinki (FI); Heikki Johannes Sipilä, Espoo (FI)

(73) Assignee: Oxford Instruments Analytical Oy (FI)

( * ) Notice: Subject to any disclaimer, the term of this patent is extended or adjusted under 35 U.S.C. 154(b) by 55 days.

(21) Appl. No.: 11/545,300

(22) Filed: Oct. 10, 2006

(65) Prior Publication Data
US 2008/0095318 A1 Apr. 24, 2008

(51) Int. Cl.
*G21K 1/04* (2006.01)
*G21K 4/00* (2006.01)
(52) U.S. Cl. .......................... 378/147; 378/44
(58) Field of Classification Search .............. 378/41, 378/44–50, 145, 147–153
See application file for complete search history.

(56) References Cited

U.S. PATENT DOCUMENTS

| | | | |
|---|---|---|---|
| 6,389,108 B1 * | 5/2002 | Ein-Gal | 378/147 |
| 6,477,226 B1 * | 11/2002 | Lehmann et al. | 378/44 |
| 7,035,372 B2 * | 4/2006 | Chen | 378/62 |
| 2004/0066902 A1 * | 4/2004 | Fraser et al. | 378/145 |

\* cited by examiner

*Primary Examiner*—Irakli Kiknadze
(74) *Attorney, Agent, or Firm*—Wood, Phillips, Katz, Clark & Mortimer

(57) ABSTRACT

An X-ray fluorescence analyzer device comprises an X-ray source and a sample window. Between the X-ray source and the sample window there are a collimator plate with a plurality of microscopic pores and an annular plate comprising material essentially opaque to X-rays. The annular plate defines an area transparent to X-rays. The pores in said collimator plate let through collimated X-rays radiated by said X-ray source towards said sample window. The area transparent to X-rays in said annular plate spatially limits in a transverse direction a beam of X-rays radiated by said X-ray source towards said sample window.

18 Claims, 4 Drawing Sheets

SELECTIVE IRRADIATION OF SMALL TARGET AREA IN X-RAY FLUORESCENT SPECTROSCOPY

TECHNICAL FIELD

The invention concerns generally the technology of irradiating a sample with X-rays for producing fluorescence. Especially the invention concerns the task of selectively irradiating a desired small target area in the sample.

BACKGROUND OF THE INVENTION

X-ray fluorescence (XRF) is an analysis method in which incident X-rays irradiate a sample, causing sample atoms to emit fluorescent radiation at characteristic wavelengths. By analysing the intensity spectrum of the received fluorescent radiation it is possible to deduce the material composition of the sample.

The X-ray source used in an XRF analyzer device is typically an X-ray tube. Due to the structure of an X-ray tube, it usually emits X-rays into a half-spherical (2*pi steradians) spatial angle from an area of the anode referred to as the focal spot. If the sample is small and/or if only a small part of the sample is to be investigated, a need arises for collimating the incident X-rays so that they only fall upon the desired target area.

Conventional X-ray collimators were made by stacking metal plates parallel to each other, leaving narrow slits between them for only radiation propagating in the desired direction to pass through. The stack of parallel metal plates must have a certain length, for example in the order of 5 cm, in the propagation direction of the X-rays in order to achieve the desired angular selectivity. This makes them ill suited for portable XRF analyzer units, where space is scarce. It is also difficult to use the metal plate stack principle for reconfigurable applications, where the angular selectivity, irradiation spot size or some similar parameter should be changed quickly and easily.

SUMMARY OF THE INVENTION

An objective of the present invention is to present a collimator arrangement for collimating incident X-rays onto a desired target area in a sample. Another objective of the invention is to present an X-ray fluorescence analyzer device utilizing such a collimator arrangement. A further objective of the invention is to minimize the space required for collimating incident X-rays in an X-ray analyzer device. A yet further objective of the invention is to present an arrangement for changing the parameters of a collimating arrangement in an X-ray fluorescence analyzer quickly and easily.

The objectives of the invention are achieved by using a thin plate with microscopic pores therethrough to realize angular selectivity, and a layer opaque to X-rays with an opening to only let through incident radiation to the desired target area.

A collimator arrangement according to the invention comprises:
- a collimator plate with a plurality of pores that penetrate through at least an essential part of the thickness of the collimator plate and that have a diameter smaller than 100 micrometers, and
- an annular plate comprising material essentially opaque to X-rays, said annular plate defining an area transparent to X-rays;

wherein said collimator plate and said annular plate are adapted to be placed in said X-ray fluorescence analyzer device between an X-ray source and a sample, and wherein said plurality of pores in said collimator plate are adapted to let through at least a part of X-rays radiated by said X-ray source, and wherein edges of said area transparent to X-rays in said annular plate are adapted to spatially limit in a transverse direction a beam of X-rays radiated by said X-ray source.

The invention concerns also an X-ray fluorescence analyzer device, which comprises:
- an X-ray source,
- a sample window to be placed adjacent to a sample, and
- between the X-ray source and the sample window a collimator plate with a plurality of pores that penetrate through at least an essential part of the thickness of the collimator plate and that have a diameter smaller than 100 micrometers, and an annular plate comprising material essentially opaque to X-rays, said annular plate defining an area transparent to X-rays;

wherein said plurality of pores in said collimator plate are adapted to let through at least a part of X-rays radiated by said X-ray source towards said sample window, and wherein edges of said area transparent to X-rays in said annular plate are adapted to spatially limit in a transverse direction a beam of X-rays radiated by said X-ray source towards said sample window.

A capillary tube has a strong collimating effect on X-rays, because X-rays only reflect at very shallow incident angles, and thus only rays the propagating directions of which are within a small range around the longitudinal axis of the capillary tube will pass through. Capillary tubes in macroscopic scale share some of the clumsiness and other drawbacks of metal plate stacks as collimators. Additionally using a long macroscopic capillary tube as a collimator means that fluctuations in focal spot location and spatial intensity become clearly visible in the characteristics of the collimated incident X-ray beam.

It is possible to produce a large number of microscopic pores through a plate having a thickness in the order from less than a millimetre to a few millimetres. A piece of such plate placed in front of an X-ray source will effectively implement accurate angular selectivity in a relatively small space. A plate with microscopic pores having the required aspect ratio can be made through etching from a semiconductor wafer. Another possibility is to fuse together a large number of glass fibres with a suitably selected core, cut a plate from the fused bunch of fibres and etch away the fibre cores.

An annular plate made of a material that is opaque to X-rays will only let those rays pass that go through the opening in the plate. Together with a collimator plate with microscopic pores such an annular plate will produce a collimator that only allows a strictly selected, highly collimated portion of incident radiation to irradiate the sample at a desired location. The annular plate can be built as an integral part of the plate with microscopic pores, or the two plates may be structurally different parts. At least one of them may be located in a movable frame, with which it is possible to move the collimator plate and/or the annular plate between a storage position and an operating position in front of the X-ray source.

The exemplary embodiments of the invention presented in this patent application are not to be interpreted to pose limitations to the applicability of the appended claims. The verb "to comprise" is used in this patent application as an open limitation that does not exclude the existence of also unrecited features. The features recited in depending claims are mutually freely combinable unless otherwise explicitly stated.

The novel features which are considered as characteristic of the invention are set forth in particular in the appended claims. The invention itself, however, both as to its construction and its method of operation, together with additional objects and advantages thereof, will be best understood from the following description of specific embodiments when read in connection with the accompanying drawings.

DETAILED DESCRIPTION OF EMBODIMENTS OF THE INVENTION

Figure 1:
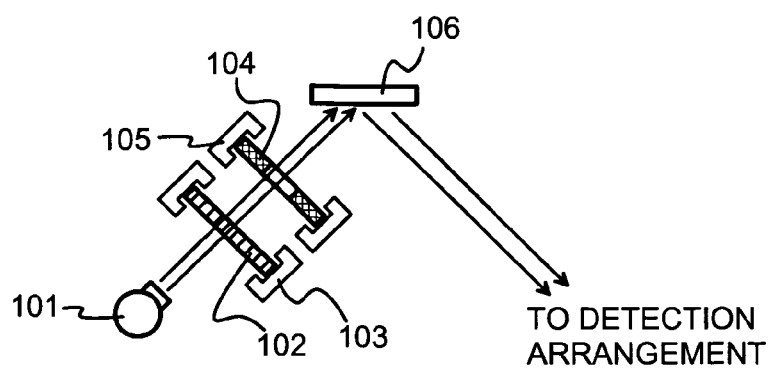
FIG. 1 illustrates a principle of using a plate with microscopic pores and an annular plate.

FIG. 1 illustrates schematically certain parts of an X-ray fluorescence analyzer device. An X-ray tube 101, which here is schematically shown as being of the side window type but which could also be of the end window type, acts as the source of incident X-rays. The incident X-rays are directed through a plate 102 that comprises a large number of microscopic pores therethrough. The microscopic pores in the plate 102 have a collimating effect, so that only X-rays the propagation direction of which is within a relatively narrow range around the longitudinal direction of the microscopic pores pass through the plate 102. A holder 103 keeps the plate 102 in place. Those incident X-rays that pass through the plate 102 meet next an annular plate 104 made of a material that is generally opaque to X-rays. The opening in the annular plate 104 lets through those X-rays that hit said opening. There is a holder 105 to keep the annular plate 104 in place. A sample 106 is shown, from which fluorescent and/or scattered X-rays go to a detection arrangement (not shown in FIG. 1).

At least two principal approaches are possible for producing the plate 102 with the microscopic pores. We will first consider the possibility of using a glass capillary plate. Glass capillary plates have conventionally been used as an image intensifiers, i.e. analog amplifying components in detecting charged particles or electro-magnetic radiation. The conventional designation of a glass capillary plate used in such applications is "microchannel plate". It consists of a glass plate with a periodic array of microscopic holes therethrough. The thickness of the glass plate is usually slightly less or slightly more than one millimeter, and a typical diameter of the holes is in the order of about ten micrometers. Thus each hole constitutes a channel through the glass plate, with an aspect ratio of typically about 100, although large deviations from these exemplary values are possible. For use as an image intensifier, the walls of the channels have been treated so that they enable the easy emission of photoelectrons and an avalanche-like multiplication of emitted electrons under the influence of an electric field between electrode metallizations on the top and bottom surfaces of the plate.

According to an aspect of the present invention, it is possible to use a glass capillary plate as such as an X-ray collimator. However, the transmission efficiency at acceptable incoming angles becomes much better, if the channel walls of a glass capillary plate are treated to act like X-ray mirrors, so that they reflect incoming X-rays instead of causing photoelectric emission. Thus each channel in the glass capillary plate acts as a miniature waveguide that exhibits high transmissivity of X-rays at a relatively narrow range of acceptable input angles around the nominal channel direction. A suitable treatment is the plating of the channel walls with a layer of a metal such as iridium, ruthenium, platinum, osmium or nickel, having a thickness of a few nanometers. An exemplary method for applying such a treatment is ALD (Atomic Layer Deposition).

Figure 2:
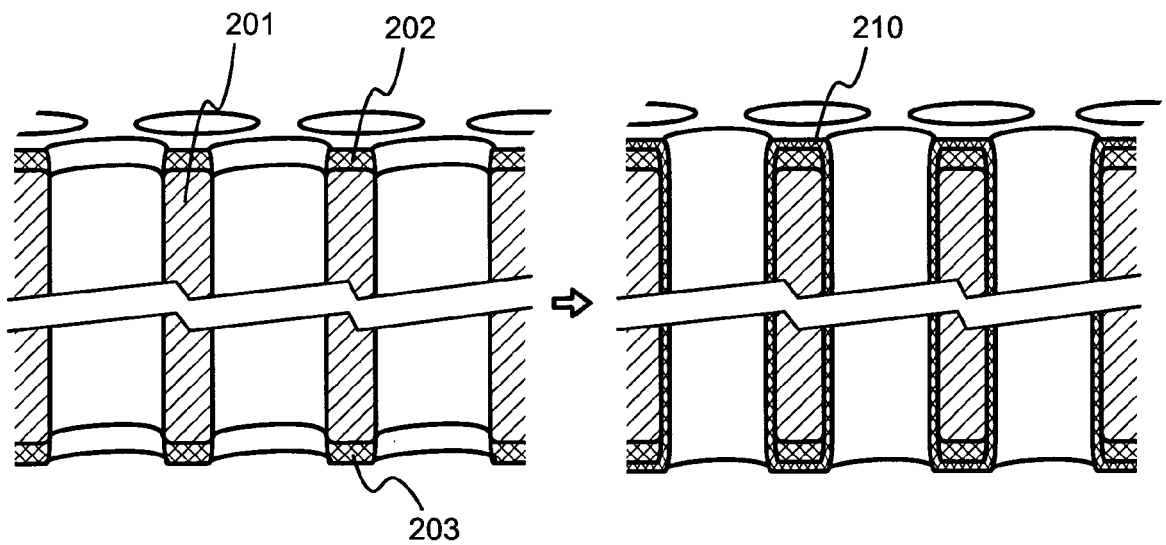
FIG. 2 illustrates the plating of the channel walls of a glass capillary plate.

FIG. 2 illustrates the principle of plating the channels of a glass capillary plate so that it becomes a better collimator for X-rays. On the left is a schematic cross section of a small portion of an ordinary glass capillary plate, of which a large part of the middle section has been omitted in order to add graphical clarity. In reality the channel length would be dozens of times larger than the channel width. The body 201 of the glass capillary plate consists of lead oxide glass or other material that is suitable for the manufacturing process. A conventional microchannel plate also comprises a top electrode layer 202 and a bottom electrode layer 203 usually made of chromium and/or nickel alloys.

On the right in FIG. 2 is a schematic cross section of a small portion of a glass capillary plate for use as an effective X-ray collimator. A very thin conformal coating 210 has been added. The thickness of the coating 210 is preferably in the order of nanometers, like 5 nanometers. In the drawing it has been vastly exaggerated: taken that the channel width is in the order of several micrometers, drawn to scale the coating 210 would be hardly visible in the drawing.

Whether or not the coating 210 also covers the top and bottom surfaces of the glass capillary plate is immaterial to the present invention. It is much more important that the coating 210 covers the walls of the channels and has as smooth a surface as possible. The smoothness requirement is one reason for not making the coating 210 thicker than a few nanometers, since the thicker the layer, the more easily its surface becomes uneven. Another reason for the small thickness of the coating 210 on the walls of the channels is that unnecessarily decreasing the channel cross-section will just reduce the transmission ratio of X-rays.

A number of important criteria are set to the material used for the coating 210. The material should have a high atomic ordinal number in order to reflect X-rays as effectively as possible. The material should be well suited for application as very thin conformal layers, using atomic layer deposition (ALD) or other suitable coating method. Additionally it is advantageous if the material of the coating 210 does not have characteristic X-ray fluorescence peaks that could be easily confused with those of analysed materials in the target. The most suitable material for the coating 210 is believed to be iridium. Other suitable materials include but are not limited to ruthenium, osmium and nickel, of which at least the last-mentioned is more suitable for application through wet chemistry than ALD. Platinum and gold are known to be applicable as X-ray mirror materials, but they may have other disadvantages that may make them a suboptimal choice for the material of the coating 210.

Figure 3:
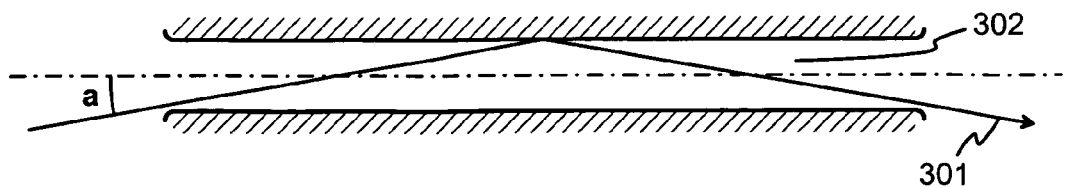
FIG. 3 illustrates the concept of an acceptable incoming angle.
Figure 4:
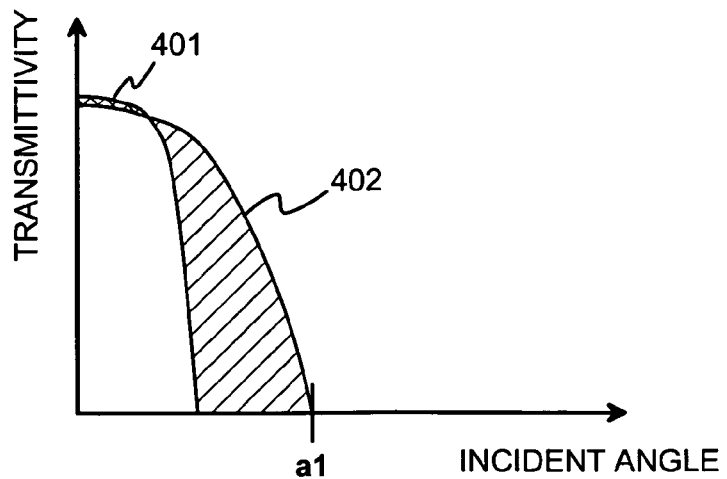
FIG. 4 illustrates the increase in acceptable incident angle due to channel plating.

FIG. 3 illustrates an X-ray 301 that enters a channel 302 in a glass capillary plate at an incident angle a that is greater than zero (here incident angle is defined as the angle between the axial direction of the channel and the propagation direction of the X-ray). If the incident angle was zero, the X-ray 301 would pass straight through the channel, assuming that it did enter the channel in the first place and did not hit some of the solid parts of the front surface of the glass capillary plate, in which case it would become absorbed. Let us first assume that the channel walls have not been plated. In that case there is some relatively small limiting value for the angle a, so that at incident angles larger than the limiting value the X-ray could not pass directly through the channel but would hit the wall instead. An unplated glass wall is not a very good reflector for X-rays, but would be very likely to cause absorption. Depicting transmittivity as a function of incident angle would give something like the qualitative curve 401 in FIG. 4.

Let us now assume that the channel walls have been plated in accordance with an aspect of the present invention. The plating allows the obliquely entering X-rays to reflect once or several times on their way through the channel, which in terms of transmittivity as a function of incident angle gives the qualitative curve 402 of FIG. 4. At a zero incident angle the transmittivity curve 402 is slightly lower than the curve 401, because the plating causes a small decrease in channel diameter and correspondingly increases the possibility of a directly coming X-ray to miss the channel and hit the front surface of the glass capillary plate instead. However, taken that the thickness of the plating is easily less than one thousandth of the channel diameter, this decrease in zero-angle transmittivity is almost infinitesimally small, and only exaggerated in FIG. 4 for clarity. On the other hand, due to the highly increased reflectivity of the channel walls, transmittivity experiences a large increase at larger values of the incident angle. The overall transmittivity of a collimator is proportional to an integral of the area that is left under the transmittivity curve in FIG. 4. The increased overall transmittivity due to better transmittivity at larger incident angles is shown with a simple hatch, while the small decrease in small-incident-angle transmittivity is shown with a cross hatch.

The applicability of a glass capillary plate with plated channel walls as a collimator comes from the fact that a collimator can well have a certain allowance function of finite width around the nominal propagating direction that should pass directly through the collimator, as long as the maximum deviation a1 from the zero incident angle, at which radiation will still pass, is not so large that it would cause serious degradation in the required degree of collimating. How wide the allowance function can be, i.e. how much a propagating direction is allowed to differ from the nominal propagating direction and still be accepted to pass the collimator, depends on the application for which the collimator is used. According to the invention, it is easy to design and manufacture collimators with differently dimensioned allowance functions by simply selecting the aspect ratio of the glass capillary plate, i.e. by selecting a suitable plate thickness (typically between 0.4 and 3 millimeters) and channel width (typically between 5 and 15 micrometers). Also the material selected for the plating of the channel walls, and the resulting degree of reflectivity of the channel walls, is a parameter to be considered when the maximum allowable value of a1 is decided. It is expected that the increase in the allowance function width will in any cases be less than two degrees compared to the allowance function of a correspondingly dimensioned glass capillary plate with unplated channels.

X-ray reflection at grazing incidence is known to be non-dispersive. This means that the collimator according to the embodiment of the invention described above does not significantly change the spectrum characteristics of the incident radiation of an X-ray fluorescence analyzer device.

Figure 5:
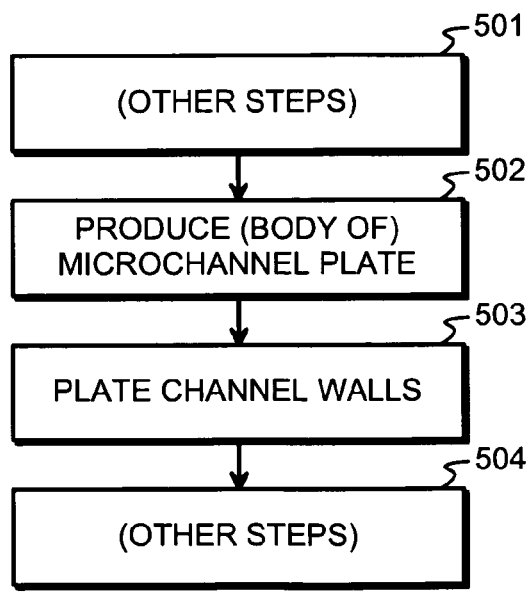
FIG. 5 illustrates some method steps of producing a glass microcapillary plate.

FIG. 5 illustrates schematically certain method steps that aim at manufacturing an X-ray collimator according to an embodiment of the invention. The process may contain some previous steps of unspecified nature, illustrated as 501. In step 502 at least the body of a glass capillary plate is produced. In a typical manufacturing process of glass capillary plates, a rod of etchable core glass is used as a support for a hollow billet of lead oxide cladding glass. A composite fibre is pulled from the combination. A number of these first draw fibres are stacked into an array, which is drawn again to produce a so-called multifiber. Several multifibres are stacked and fused together under vacuum, which results in a thick rod-like product known as a boule. The boule is sliced and polished to the required thickness and outline of the desired glass capillary plates. The solid cores, which at this stage still perforate the plate, are etched away, thus producing the characteristic array of microscopic holes through the plate.

A complete manufacturing process of conventional microchannel plates involves firing the plates in a hydrogen oven to produce a semiconducting surface layer with the de-sired resistance and secondary electron yield, as well as producing the top and bottom electrode layers. For the purposes of the present invention these are un-necessary steps and can be left out. However, they do not cause much change either to the operation of the glass capillary plate as an X-ray collimator, so concerning the present invention it is immaterial, whether step 502 of the manufacturing process includes the hydrogen firing and electrode producing sub-steps or not.

Step 503 involves plating the channel walls with the thin coating reflective of X-rays, for example in an ALD process. Other method steps may follow after that as is illustrated as 504.

A microchannel plate meant for use as a particle detector or image intensifier has often a so-called nonzero bias angle, which means that the channels are not perpendicular to the planar surfaces of the plate. The bias angle is selected in step 502 mentioned above, by tilting the blade that is used to cut slices from the boule (or by tilting the boule with respect to the blade). If a glass capillary plate with plated channel walls is to be used as a collimator according to an embodiment of the invention, it should either have a zero bias angle, or the glass capillary plate should be placed at a non-perpendicular angle with respect to the desired propagation direction of X-rays, so that the channel direction coincides with the desired propagation direction of X-rays.

The second principal approach for producing the plate 102 with the microscopic pores in FIG. 1 is to use a semiconductor wafer or a corresponding piece of etchable solid material as the starting point. From prior art there is known a general principle of using an anisotropically etched silicon semiconductor plate as the collimator for the scattered X-rays or fluorescent X-rays somewhere along the radiation path from the sample to a detector. A prior art publication U.S. Pat. No. 6,477,226 suggests anisotropically etching deep pores of diameter between 0.1 and 100 micrometers to a semiconductor plate. The publication suggests either leaving a thin layer of the semiconductor material intact at the bottom of the pores, or lining the inside of each pore with a so-called stabilizing layer made of silicon nitride, silicon carbide, boron nitride, boron hydride, boron carbide and/or carbon, after which the remaining thin semiconductor layer could be removed, which leaves the previously closed end of each pore visible but covered with the stabilizing layer material.

The materials that said publication suggests for the stabilizing layer have the drawback that they do not function as X-ray mirrors. The performance of a collimator plate made of a semiconductor material and having a plurality of micropores anisotropically etched therethrough could be remarkably improved by using an additional coating of iridium, ruthenium, osmium, platinum, nickel, or gold either instead of the so-called stabilizing layer of said prior art publication or on top of it.

We should also note that silicon is relatively transparent to X-rays, which means that the silicon-based collimator plates known from prior art would hardly be suitable for collimating incident radiation. The intensity of the radiation produced by the X-ray source is simply so high that a significant portion of the rays propagating in other directions than those that a collimator should let through would also penetrate through the solid silicon parts that constitute the structural matrix of the plate. However, germanium is a substrate that lends itself easily to anisotropic etching, and that is relatively easily available in wafer thicknesses suitable for collimator plates. Germanium is also very seldom among those elements that should be analysed from a sample, so it is unlikely that excited spectral lines or scattered radiation from germanium would interfere with the measurement.

In the following we will use the designation "collimator plate" to mean either a glass capillary plate based collimator plate or a semiconductor (preferably germanium) based collimator plate with a plurality of (preferably iridium-coated) microscopic pores therethrough.

Figure 6:
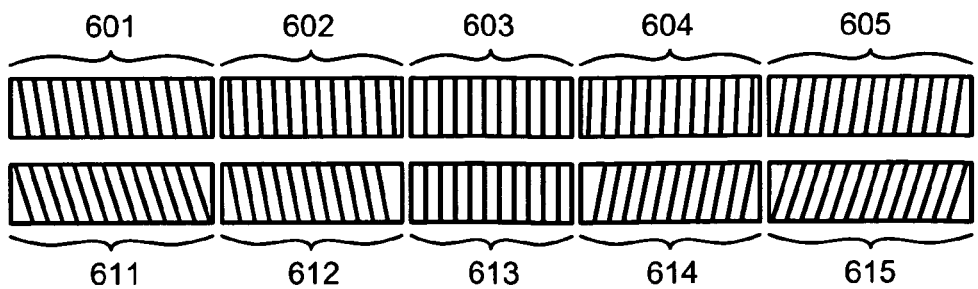
FIG. 6 illustrates an array of collimator plate sections with different bias angles.

FIG. 6 is a cross section that shows how an assembly of collimator plates with differently directed channels therethrough can be used as a combined collimator and focusing lens for X-rays. We assume that radiation comes from top to down. The upper row of collimator plate sections has a central plate 603 with zero bias angle. On each side of it there are plates 602 and 604, with small bias angles of equal absolute magnitude but opposite sign. The utmost plates 601 and 605 constitute a similar pair, having bias angles of equal absolute magnitude but opposite sign, said magnitude being slightly larger than that of plates 602 and 604. In the lower row the same principal arrangement is repeated, with the central plate 613 having zero bias angle, the intermediate plates 612 and 614 constituting an equal-magnitude and opposite-sign pair and the utmost plates 611 and 615 likewise. The increasing steps in the absolute value of the bias angle are larger in the lower row, with plates 611 and 615 having the largest absolute bias angle magnitude in the whole assembly.

Figure 7:
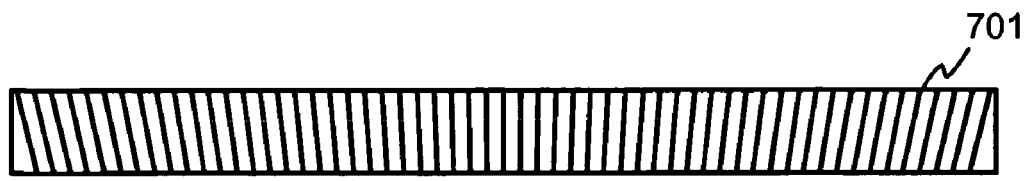
FIG. 7 illustrates a collimator plate with varying bias angle.
Figure 8:
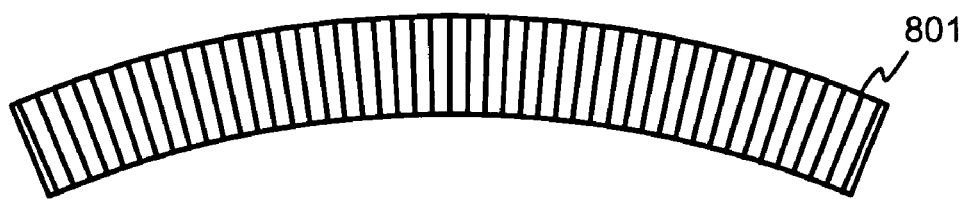
FIG. 8 illustrates a curved collimator plate.

X-rays that pass through the collimator plate assembly of FIG. 6 from top to down will experience certain convergence that directs them at least approximately towards a point or area of convergence located further down. Similar lens-like effects are achieved if the manufacturing process of the collimator plate allows the bias angle to be gradually changed across the plate like in the plate 701 of FIG. 7, or if a collimator plate with initially parallel channels is afterwards made to exhibit some curvature like plate 801 in FIG. 8. Collimator plates and collimator plate arrangements that include a focusing characteristic, like the ones shown in FIGS. 6, 7, and 8, can be said to be special cases of the concept "collimator", because they still act as pure collimators at least for those X-rays that pass through the central region (or more generally: the region where the channel direction is the same as the incident direction of those X-rays that should pass), and because they only allow X-rays with incident propagating directions within the (relatively narrow) allowance function to pass. Thus also the embodiments shown in FIGS. 6, 7, and 8 fall within the scope of the claims directed to a collimator. It should be noted that for reasons of graphical clarity, the differences in bias angle and the curvature of the collimator plate in FIG. 8 have been exaggerated.

Figure 9:
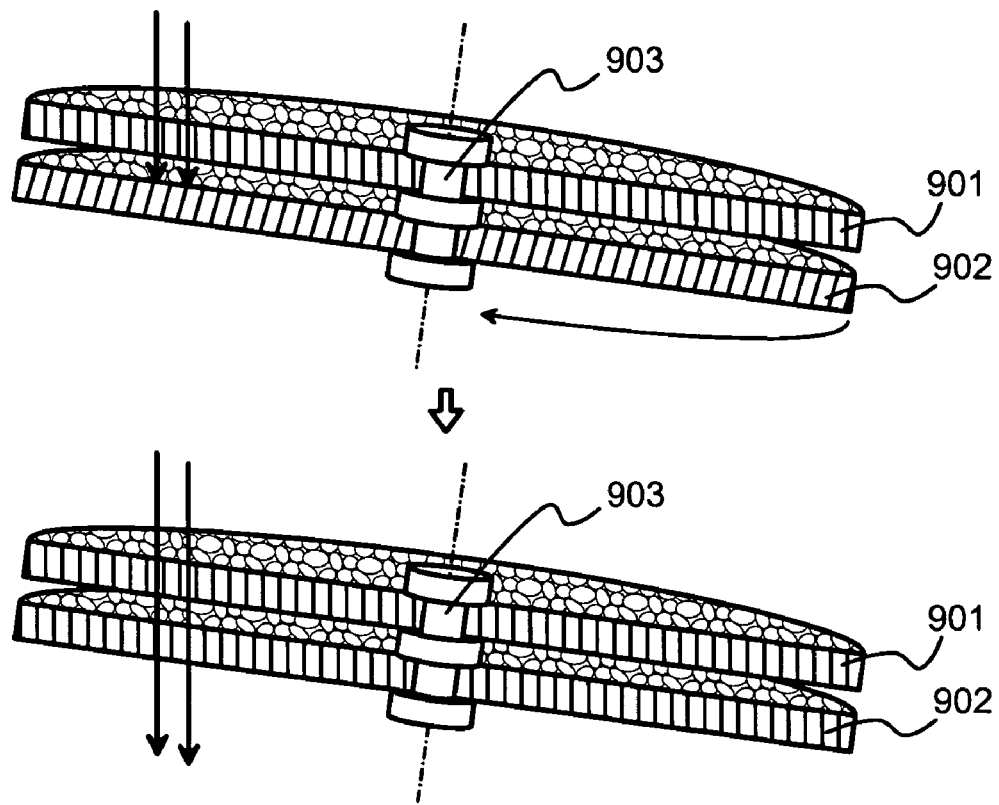
FIG. 9 illustrates a variable X-ray attenuator made of two collimator plates.

Two consecutive collimator plates can be used to implement a variable-attenuation X-ray attenuator that also has a collimating effect. This requires there to be a possibility of causing relative movement between the two collimator plates, so that in one relative position the channel direction in both collimator plates is essentially the same and in some other relative position the channel direction in the collimator plates is not the same. In practice this principle can be implemented for example in the way shown in FIG. 9. A first collimator plate 901 and a second collimator plate 902 have an equal, non-zero bias angle. Both collimator plates are assumed to be round, but are shown in FIG. 9 schematically as cut through to illustrate the concept of channel direction. The planar direction of both collimator plates is the same. At least one of them, here the second collimator plate 902, can be rotated around an axis 903 that is perpendicular to said planar direction of the collimator plates.

In one rotational position, shown in the upper part of FIG. 9, the channel direction in the second collimator plate 902 differs so much from the channel direction in the first collimator plate 901 that at least a majority of X-rays that pass through the first collimator plate 901 cannot pass through the second collimator plate 902, due to the difference in channel direction between the collimator plates. In another rotational position, shown in the lower part of FIG. 9, the channel direction in the second collimator plate 902 is essentially the same as the channel direction in the first collimator plate 901 that at least a majority of X-rays that pass through the first collimator plate 901 also pass through the second collimator plate 902. Since the transmittivity of both plates as a function of incident angle has a finite width around the nominal channel direction, between the position shown in the upper and lower parts of FIG. 9 there are a number of intermediate positions in which the relative amount of X-rays coming through varies between these extremities.

Figure 10:
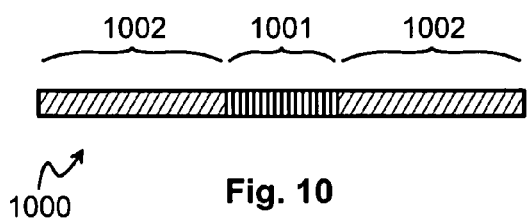
FIG. 10 illustrates a plate that acts both as a collimator plate and an annular plate.

A collimator plate alone does not limit the cross section of the incident radiation beam. According to an aspect of the invention, an annular plate or layer can be used together with the collimator plate to achieve the desired incident radiation beam with a limited width. Various ways exist for combining the use of a collimator plate and an annular plate or layer. FIG. 10 is a cross section of a plate 1000, a middle section 1001 of which comprises a number of microscopic pores through the plate, with their walls preferably coated with X-ray-reflecting material. The edge sections 1002 of the plate 1000 are without said microscopic pores, so that the body of the plate 1000 also constitutes the annular plate or layer referred to above. Since the middle section 1001 is not actually an opening in the same sense as in the other annular plates discussed in this description, we may generalize the definition of an annular plate so that it defines an area transparent to X-rays, which in true annular plates is an opening and in combined embodiments like that of FIG. 10 is the section that comprises the microscopic pores.

Figure 11:
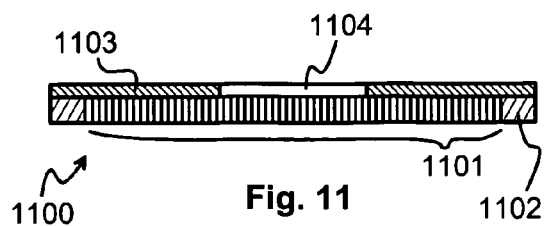
FIG. 11 illustrates an annular plate on the surface of a collimator plate.

FIG. 11 illustrates another alternative embodiment, in which a collimator plate 1100 has a (relatively wide) middle section 1101 with pores and only a narrow edge section 1102 without pores, for making it easier to attach the collimator plate 1100 to a holder (not shown). It would not be necessary to have any edge section at all. On one surface of the collimator plate 1100 there is an annular layer 1103 of a material essentially opaque to X-rays. At its center the annular layer 1103 defines an opening 1104. The dimensions of the opening 1104 define, how wide is the collimated X-ray beam that will come through the collimator plate 1100. The annular layer 1103 may be formed as an integral layer of the collimator plate 1100, for example by applying a suitable annular metallization pattern of sufficient thickness to one side of the collimator plate. Alternatively the annular layer 1103 may originally be a mechanically different component that is just stacked together with the collimator plate and possibly attached thereto by glueing, soldering or other means.

Figure 12:
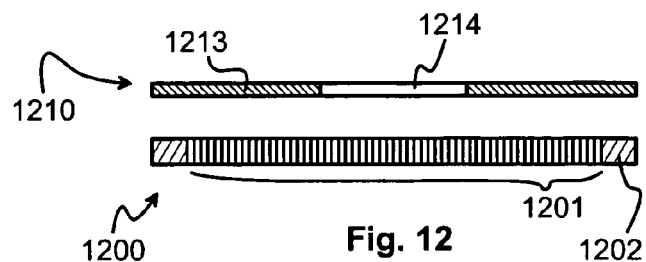
FIG. 12 illustrates a collimator plate and a separate annular plate.

FIG. 12 illustrates yet another alternative embodiment, in which the collimator plate 1200 and an annular plate 1210 are separate mechanical entities and can be separately attached to corresponding holders (not shown). A section 1201 of the collimator plate 1200 is equipped with microscopic pores, with their walls preferably coated with X-ray-reflecting material. The collimator plate 1200 may have a solid edge section 1202 for making attachment to holder easier, but this is not necessary. The body of the annular plate 1210 constitutes an annular barrier 1213 essentially opaque to X-rays, and defines an opening 1214 for the X-rays to come through. Together the collimator plate 1200 and the annular plate 1210 are configured to both collimate and spatially limit an incident X-ray beam.

Figure 13:
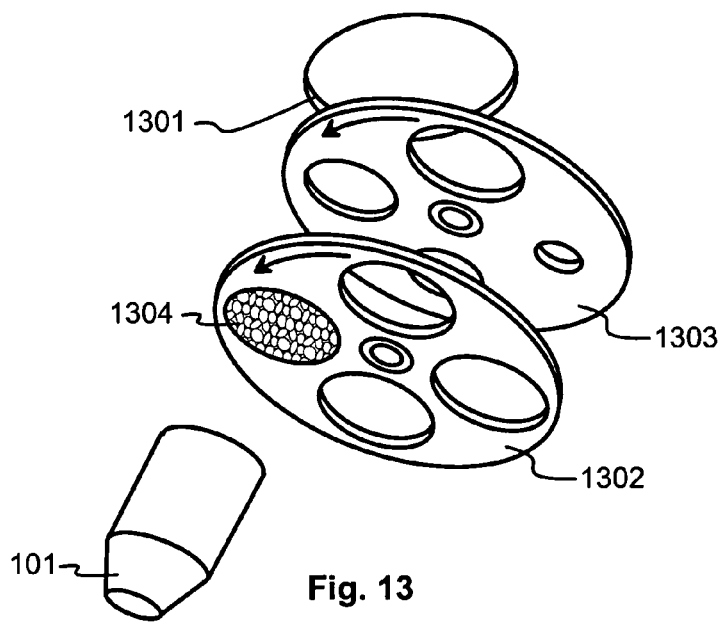
FIG. 13 illustrates using movable holders in an analyzer device.

Since not all X-ray fluorescence measurements require a well collimated and spatially limited incident X-ray beam, it is in many cases advantageous to equip an X-ray fluorescence analyzer device with a mechanism that allows easily selecting into use the incident-beam-shaping means that are needed. FIG. 13 illustrates schematically certain parts of an X-ray fluorescence analyzer device, in which an X-ray tube 101 of the end window type acts as the source of incident X-rays. Within the space between the X-ray source and a sample window 1301 of the analyzer device there are located a first movable holder 1302 and a second movable holder 1303. The first movable holder 1302 comprises at least one location in which resides a collimator plate 1304. The form of the first movable holder 1302 shown here (a circular plate rotatable around its central normal axis, and with circular openings for attaching collimator plates and/or other equipment) is naturally only exemplary. From the technology of X-ray fluorescence analyzers it is known to use movable holders of various kinds for selectively placing e.g. exchangeable filters to the path of the incident X-rays. The other circular openings of the first movable holder 1302 may comprise such filters.

The second movable holder 1303 is configured to offer into use various annular openings so that the transverse dimensions of the incident X-ray beam can be limited to the desired size. This can be accomplished either so that there is one or more attachment locations in the second movable holders into which the user may removably attach separate annular plates according to need, or like in FIG. 13 in which the second movable holder 1303 itself constitutes the annular plate by having a number of differently dimensioned openings therethrough.

If the X-ray fluorescence analyzer only comprises a single movable holder, it is most advantageous to use a combined structure of a collimator plate and an annular layer like that shown in FIG. 11 and to attach it to a suitable location in the movable holder. Alternatively, especially in the absence of a second movable holder, a changeable annular plate can be constructed from a number of partially overlapping, radially movable parts in the same way as the controllable aperture is implemented in a systems camera.

The invention allows incident X-rays to be directed to a relatively small area in the sample. The irradiated sample area has essentially the same form and dimensions as the opening in the annular plate. A natural exception occurs if the incident X-ray beam comes at an oblique angle to the sample, in which case the irradiated sample area is the area the projection of which, looked from the direction of the incident X-rays, has the form and dimensions of the opening in the annular plate. The invention does not limit the selection of the form and dimensions of the opening in the annular plate. In exemplary cases the invention could be used to only irradiate a spot-like sample area with transverse dimensions in the order of a millimeter or a couple of millimeters with incident X-rays.

Figure 14:
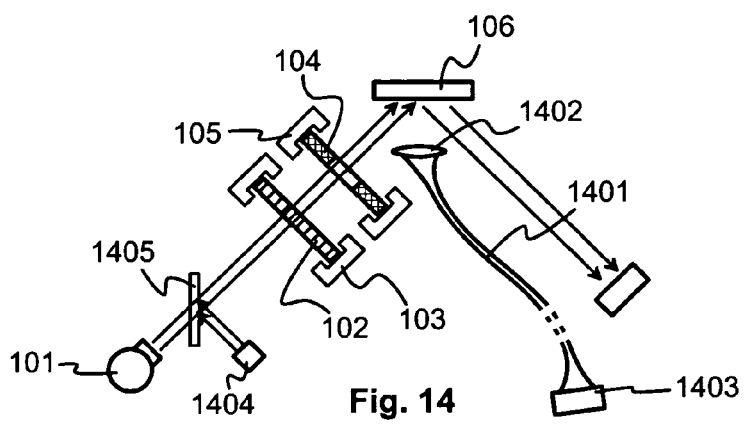
FIG. 14 illustrates an analyzer device with illuminating means and an optic aiming aid.

In order to help a human user to perceive, what part of the sample will be subjected to incident X-rays, it is advantageous if the X-ray fluorescence analyzer device includes an optical aiming aid. FIG. 14 illustrates schematically certain considerations related to optical aiming aids. The X-ray fluorescence analyzer device of FIG. 14 comprises a fiber optic sight generally designated as 1401, with an objective 1402 aimed to look at the sample 106 and an ocular or display 1403 for conveying a visual image to a human user. Using the fixed structures of the X-ray fluorescence analyzer device to aim and attach the objective 1402 accurately enough may as such be enough for ensuring that the user gets a good perception of which area of the target will be irradiated with incident X-rays.

In addition the X-ray fluorescence analyzer device of FIG. 14 comprises a light source 1404 and a mirror 1405, which may be either a dichroic mirror that reflects visible light but lets X-rays through, or a movable mirror that can be moved to the location seen in FIG. 14 for the duration of optical aiming. Together the light source 1404 and the mirror 1405 produce a beam of visible light, which comes from the same direction and through the same collimating and spatial limiting means as the beam of incident X-rays. Thus the sample area illuminated with visible light from the light source 1404 will be exactly the same as the sample area irradiated with incident X-rays from the X-ray tube 101. The user sees, which part of the sample is illuminated, through the fiber optic sight 1401. Illumination of the appropriate sample area with visible light can be accomplished also with other kinds of arrangements, for example with a fiber optic illumination system either integrated with the fiber optic sight 1401 or built separately.

We claim:

1. An arrangement for collimating a beam of incident X-rays in an X-ray fluorescence analyzer device, comprising:
    a collimator plate with a plurality of pores that penetrate through at least an essential part of the thickness of the collimator plate and that have a diameter smaller than 100 micrometers, and
    an annular plate comprising material essentially opaque to X-rays, said annular plate defining an area transparent to X-rays;
    wherein said collimator plate and said annular plate are adapted to be placed in said X-ray fluorescence analyzer device between an X-ray source and a sample, and wherein said plurality of pores in said collimator plate are adapted to let through at least a part of X-rays radiated by said X-ray source, and wherein edges of said area transparent to X-rays in said annular plate are adapted to spatially limit in a transverse direction a beam of X-rays radiated by said X-ray source, and wherein walls of at least some of said pores comprise a coating, the material of the coating being one of: iridium, ruthenium, osmium, platinum, gold.

2. An arrangement according to claim 1, wherein said collimator plate is a glass capillary plate, a body of which is made of lead oxide glass.

3. An arrangement according to claim 1, wherein said collimator plate is a semiconductor wafer with a plurality of anisotropically etched pores therethrough.

4. An arrangement according to claim 3, wherein the semiconductor material of said wafer is germanium.

5. An arrangement according to claim 1, wherein said annular plate is an edge section of the collimator plate, so that said area transparent to X-rays is a section of said collimator plate where said pores are located.

6. An arrangement according to claim 1, wherein said annular plate is an annular layer of a material opaque to X-rays, attached to one surface of said collimator plate.

7. An arrangement according to claim 1, wherein said collimator plate and said annular plate are separate mechanical entities.

8. An arrangement according to claim 7, wherein said annular plate defines a plurality of openings with different dimensions, and said annular plate is adapted to be moved in relation to said collimator plate in order to selectively make a desired one of said plurality of openings coincide with at least a part of said collimator plate.

9. An arrangement according to claim 1, comprising two collimator plates in sequence, each of them having a certain direction of pores that pass through at least an essential part of the thickness of the respective collimator plate, wherein at least one of said two collimator plates is movable between a first position, in which the direction of pores in said one of said two collimator plates is different from the direction of pores in the other collimator plate, and a second position, in which the direction of pores in said one of said two collimator plates is the same as the direction of pores in the other collimator plate.

10. An X-ray fluorescence analyzer device, comprising:
    an X-ray source,
    a sample window to be placed adjacent to a sample, and
    between the X-ray source and the sample window a collimator plate with a plurality of pores that penetrate through at least an essential part of the thickness of the collimator plate and that have a diameter smaller than 100 micrometers, and an annular plate comprising material essentially opaque to X-rays, said annular plate defining an area transparent to X-rays;
    wherein said plurality of pores in said collimator plate are adapted to let through at least a part of X-rays radiated by said X-ray source towards said sample window, and wherein edges of said area transparent to X-rays in said annular plate are adapted to spatially limit in a transverse direction a beam of X-rays radiated by said X-ray source towards said sample window, and wherein walls of at least some of said pores comprise a coating, the material of the coating being one of: iridium, ruthenium, osmium, platinum, gold.

11. An X-ray fluorescence analyzer device according to claim 10, wherein said collimator plate is a glass capillary plate, a body of which is made of lead oxide glass.

12. An X-ray fluorescence analyzer device according to claim 10, wherein said collimator plate is a semiconductor wafer with a plurality of anisotropically etched pores therethrough.

13. An X-ray fluorescence analyzer device according to claim 12, wherein the semiconductor material of said wafer is germarnum.

14. An X-ray fluorescence analyzer device according to claim 10, comprising a movable holder mechanism that is movable between a first position, in which at least one of said collimator plate and said annular plate is between the X-ray source and the sample window, and a second position, in which said at least one of said collimator plate and said annular plate is not between the X-ray source and the sample window.

15. An X-ray fluorescence analyzer device according to claim 14, wherein in said second position said movable holder mechanism is configured to hold a filter between the X-ray source and the sample window.

16. An X-ray fluorescence analyzer device according to claim 10, comprising an optical aiming aid configured to convey to a display means an optical image of a target area of a sample brought adjacent to the sample window.

17. An X-ray fluorescence analyzer device according to claim 16, comprising an illumination means configured to illuminate said target area in said sample with visible light.

18. An arrangement for collimating a beam of incident X-rays in an X-ray fluorescence analyzer device, comprising:
    a collimator plate with a plurality of pores that penetrate through at least an essential part of the thickness of the collimator plate and that have a diameter smaller than 100 micrometers, and
    an annular plate comprising material essentially opaque to X-rays, said annular plate defining an area transparent to X-rays;
    wherein said collimator plate and said annular plate are adapted to be placed in said X-ray fluorescence analyzer device between an X-ray source and a sample, and wherein said plurality of pores in said collimator plate are adapted to let through at least a part of X-rays radiated by said X-ray source, and wherein edges of said area transparent to X-rays in said annular plate are adapted to spatially limit in a transverse direction a beam of X-rays radiated by said X-ray source, and wherein said collimator plate is a germanium wafer with a plurality of anisotropically etched pores therethrough.

* * * * *